United States Patent [19]

Leighton

[11] Patent Number: 5,088,980
[45] Date of Patent: Feb. 18, 1992

[54] INTRA-URETHRAL VALVE WITH INTEGRAL SPRING

[75] Inventor: Stephen B. Leighton, Maplewood, N.J.

[73] Assignee: The United States of America as represented by the Department of Health and Human Services, Washington, D.C.

[21] Appl. No.: 530,585

[22] Filed: May 31, 1990

[51] Int. Cl.$^5$ .............................................. A61F 2/02
[52] U.S. Cl. .............................. 600/30; 128/DIG. 25; 604/247; 604/256
[58] Field of Search .................................. 600/29–31; 128/DIG. 25; 604/247, 256

[56] References Cited

U.S. PATENT DOCUMENTS

| | | |
|---|---|---|
| 2,638,093 | 5/1953 | Kulick . |
| 3,372,695 | 3/1968 | Beliveau et al. . |
| 3,903,894 | 9/1975 | Rosen et al. . |
| 4,167,952 | 9/1979 | Reinicke . |
| 4,209,010 | 6/1980 | Ward et al. . |
| 4,222,377 | 9/1980 | Burton . |
| 4,386,601 | 6/1983 | Trick . |
| 4,553,533 | 11/1985 | Leighton ................ 600/30 |
| 4,828,554 | 5/1989 | Griffin .................... 604/247 |

Primary Examiner—David J. Isabella
Assistant Examiner—K. Reichle
Attorney, Agent, or Firm—Lowe, Price, LeBlanc & Becker

[57] ABSTRACT

A prosthetic urethral sphincter valve with an integral spring valve member which comprises an elastic valve element having an upper portion which defines a central fluid passage and a lower diaphragm portion which includes a rolling diaphragm. The prosthetic urethral sphincter valve is placed totally within a patient's urethra. The lower diaphragm portion of the elastic valve element includes a tapered wall structure which provides for a spring action which demonstrates a non-linear force curve. The central fluid passage assumes a kinked or closed position, or a straighten or open position depending upon the position of the rolling diaphragm. Applied bladder pressure effects the position of the rolling diaphragm and thus the opening and closing of the central fluid passage.

16 Claims, 3 Drawing Sheets

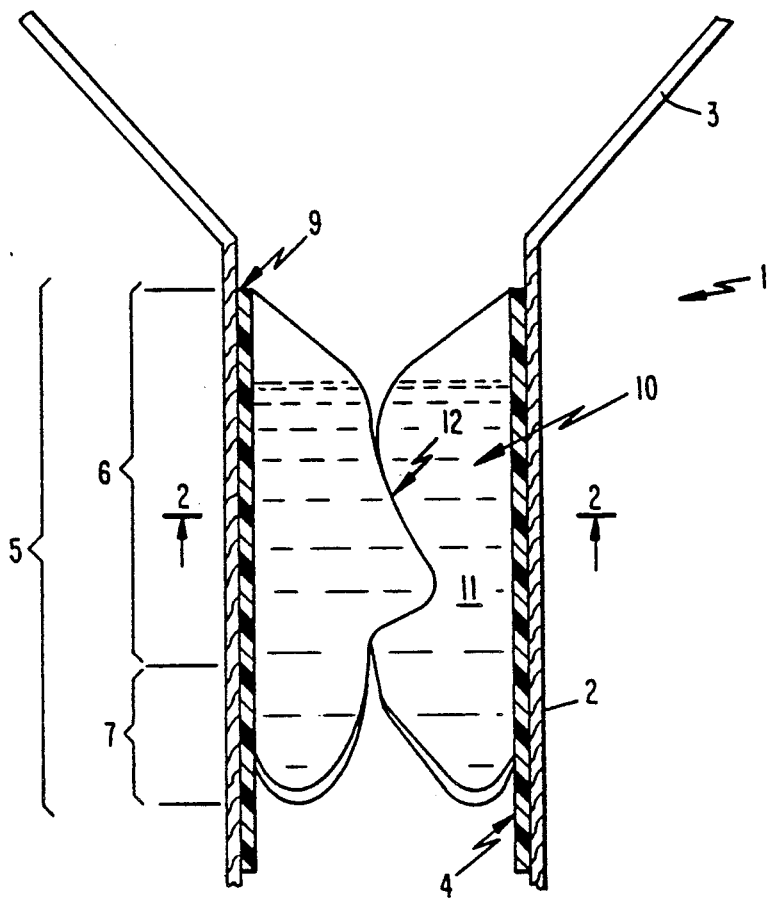
Figure 1
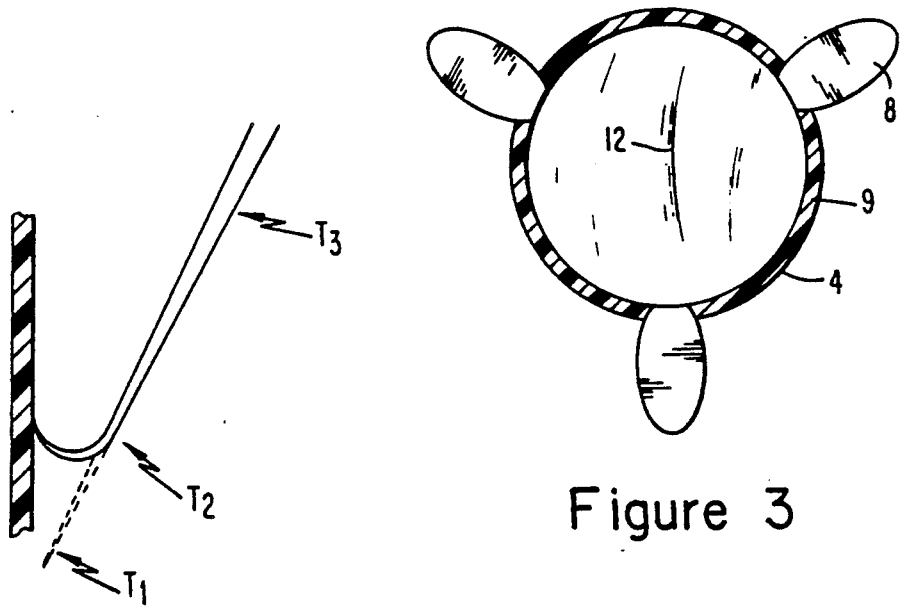
Figure 2
Figure 3

INTRA-URETHRAL VALVE WITH INTEGRAL SPRING

TECHNICAL FIELD

The present invention relates to prosthetic urethral valves for controlling urinary continence. More particularly, the present invention relates to a prosthetic urethral valve having an integral spring member which may be installed totally within a patient's urethra without surgery, and which is controlled by the patient's voluntary elevation of bladder pressure substantially in a normal manner.

BACKGROUND ART

Prosthetic urethral valves of the prior art for incontinent patients involve numerous disadvantages. Most urethral valves of the prior art utilize an inflatable cuff around the outside of the urethra, or a catheter that extends beyond the distal end of the urethra. The former type of urethral valve requires surgery for installation, and the latter type is noncosmetic and invites infection. Also, a number of the previously proposed urethral valve devices must be operated externally and therefore are dependent on manual intervention.

Exemplary prior art devices which suffer from the above-discussed disadvantages are disclosed in U.S. Pat. Nos. 2,638,093 to Kulick; 3,372,695 to Beliveau; 3,903,894 to Rosen et al; 4,167,952 to Reinicke; 4,209,010 to Ward et al; 4,222,377 to Burton; 4,256,903 to Helms et al; and 4,386,601 to Trick.

A more recent intra-urethral prosthetic sphincter valve is disclosed in U.S. Pat. No. 4,553,533 to the present inventor. This device solves many of the disadvantages associated with prior devices, but utilizes a linear spring characteristic which requires a patient to exert increased pressures to maintain the opening of the valve element.

There remains a definite need for a non-surgically installed prosthetic urethral valve which has functional sensitivity to the natural physiological sustained internal bladder pressure produced voluntarily by the patient.

DISCLOSURE OF THE INVENTION

It is accordingly one object of the present invention to provide for improved artificial sphincter control.

Another object of the present invention is to provide an improved prosthetic urethral valve which overcomes the disadvantages and deficiencies of previously known devices for controlling a patient's urinary continency.

A further object of the present invention is to provide an improved urethral valve having an integral spring element which can be installed totally within the urethra of a patient without surgery.

A further object of the present invention is to provide an improved urethral valve which closely simulates natural physiologic functions.

A still further object of the present invention is to provide an improved urethral valve which opens in response to substantially normal voluntary elevation of the bladder pressure of a patient but which does not open in response to momentary natural elevation of bladder pressure due to coughing, jumping, or the like.

A still further object of the present invention is to provide an improved prosthetic urethral valve which can be totally installed in the patient's urethra without surgery, which is cosmetically normal, which minimizes the risk of infection, which provides normal, substantially positive sealing action, which opens responsive to sustained elevation of bladder pressure, and which slowly returns to a closed state after release of bladder pressure.

An even further object of the present invention is to provide for a method for controlling urinary continence of a patient.

According to the present invention there is provided a prosthetic urethral sphincter valve which comprises a rigid tubular casing adapted to be placed in a patient's urethra with its top end portion located adjacent and exposed to the patient's bladder and an integral elastic valve member which comprises a central passage, means to open the central passage by the application of a first force $F_1$, and means to maintain the open position of the central passage by the application of a second force $F_2$, wherein $F_1 > F_2$.

The present invention further provides for a prosthetic urethral sphincter valve comprising a rigid tubular casing adapted to be placed in a patient's urethra with its top end portion located adjacent and exposed to the patient's bladder and an elastic valve member located within the rigid tubular casing and comprising an upper portion which defines a central tubular passage and a lower diaphragm portion which comprises a rolling diaphragm.

Also provided by the present invention is a method of controlling urinary continence of a patient which comprises positioning a rolling diaphragm valve element in the urethra of the patient, whereby under normal bladder pressure the rolling diaphragm valve element closes a central fluid passage which may be opened by the patient by exerting bladder pressure on the rolling diaphragm.

BRIEF DESCRIPTION OF DRAWINGS

The present invention will now be described with reference to the annexed drawings, which are given by way of non-limiting examples only in which:

FIG. 1 is an enlarged vertical cross-sectional view taken axially through a prosthetic urethral valve according to the present invention, shown installed in the upper end portion of a patient's urethra, and shown in a normal sealing configuration.

FIG. 2 is an enlarged sectional view showing the varying wall thickness of the lower diaphragm portion of the elastic valve member near the cylindrical casing of the valve assembly.

FIG. 3 is a horizontal cross-sectional view taken substantially on line 2—2 of FIG. 1.

BEST MODE FOR CARRYING OUT THE INVENTION

Figure 4:
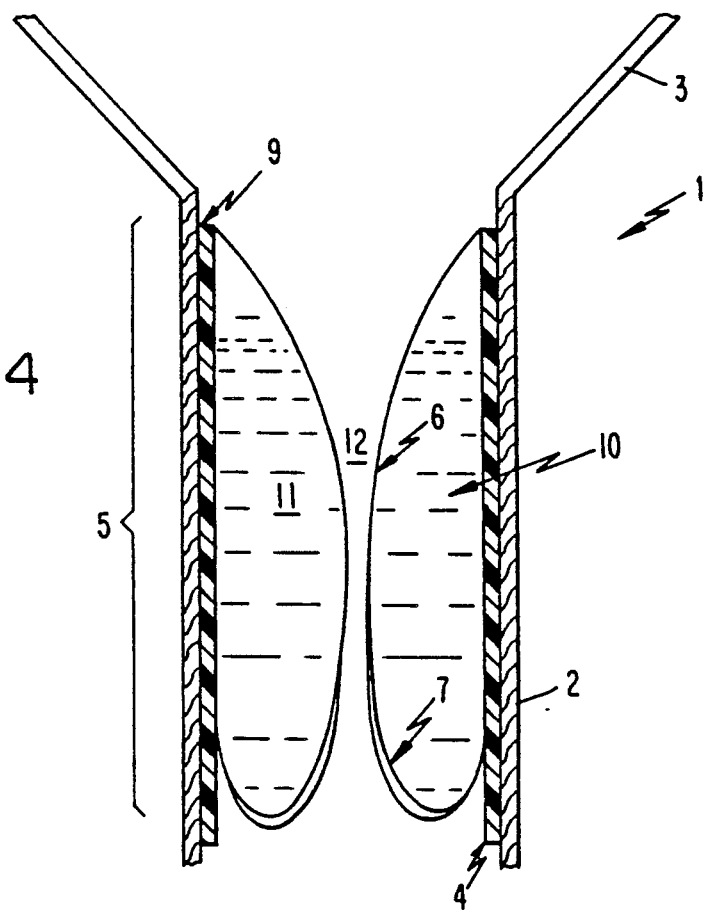
FIG. 4 is an enlarged vertical cross-sectional view taken axially through a prosthetic urethral valve according to the present invention similar to that of FIG. 1, but showing the valve in an open state responsive to the patient's sustained elevation of the bladder pressure.

The present invention involves a prosthetic urethral sphincter valve assembly which is designed to be totally inserted in a patient's urethra. The assemble includes a rigid tubular casing which is adapted to be placed in a patient's urethra with the top end portion of the casing located adjacent and exposed to the patient's bladder. Retaining means in the form of outwardly extending petals are attached to the upper surface to the casing to insure retention of the assembly in the proper position in the patient's urethra.

An elastic valve member is located within the rigid tubular casing and includes an upper portion which defines a central tubular passage and a lower diaphragm portion which comprises a rolling diaphragm. An annular region between the rigid tubular casing and the elastic valve member is filled with a viscous fluid to dampen the movement of the elements.

The rolling diaphragm at the lower portion of the elastic valve member, as discussed in detail below, has the shape of a slightly tapered cone which is partially turned inside out and attached to the inner surface to the casing. The rolling diaphragm portion of the elastic valve member has a wall which has two successive tapered portions described in detail below which effect the opening and closing of the central fluid passage defined by the upper portion of the elastic valve element.

Forces acting on the rolling diaphragm effect the configuration of the central fluid passage defined by the upper portion of the elastic valve element, whereby the central fluid passage is either "kinked" in a closed position, or straightened in a opened position.

Referring to the drawings, 1 generally designates the improved prosthetic urethral valve assembly according to the present invention, shown installed in the upper end portion of a patient's urethra 2 and extending into the patient's bladder 3. The valve assembly 1 comprises a rigid tubular casing 4 made of a suitably strong material which is both biocompatible and resistant to corrosion or degradation in a urine environment, e.g., stainless steel or plastic.

The valve element utilized in the improved prosthetic urethral valve assembly of the present invention comprises an elastic valve member 5 which includes an upper portion 6 and an integral lower diaphragm portion 7. As suggested in FIG. 4, the elastic valve member is cast or molded in the form of a slightly tapered cone, with the upper portion 6 having thin tubular walls and the lower diaphragm portion having thicker tapered walls.

Figure 7:
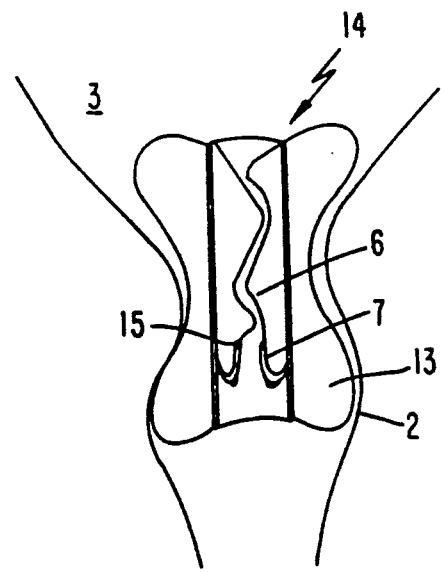
FIG. 7 is an enlarged sectional view showing a prosthetic urethral valve according to the present invention held in position in a patient's urethra by a balloon positioning and retaining means.

A plurality of evenly angularly spaced resilient retaining petal members 8 are fixedly secured to the outer upper surface 9 of the rigid tubular casing 4 in outwardly and upwardly divergent relationship to the top of rigid tubular casing 4. The resilient retaining petal members 8 are flatly retentively engageable with the upwardly divergent bottom wall surface of the bladder 3 to hold the prosthetic sphincter valve assembly 1 in the working position thereof as illustrated in FIG. 1. The resilient petal members 8 are sufficiently flexible to be squeezed inwardly enough to permit insertion of the valve assembly 1 into the urethra 2 and to allow it to be pushed upwardly in the urethra to its working position. In an alternate embodiment, an inflatable balloon may be used in place of the petal members 8. Such a balloon 13 is illustrated in FIG. 7 as having an outer hourglass shape and a central opening 14 in which the prosthetic urethral valve assembly 1 is positioned. FIG. 7 further illustrates an optional joining and isolation ring 15 that may be utilized to connected the upper and lower diaphragm portions of the elastic valve element in an alternate embodiment in which they are not integral.

An annular space 10 generally located between the cylindrical casing and the elastic valve member is filled with a relatively viscous fluid such as a liquid, grease or gel 11, such as viscous silicone grease. The viscous liquid, grease or gel functions to provide a degree of resistance to changes of shape of the elastic valve member 5. In this manner, the viscous fluid provides a damping effect to the operation of the valve assembly.

During assembly, the upper portion of the elastic valve member 6 is fastened within the rigid tubular casing 4 adjacent the upper end thereof 9. The lower diaphragm portion 7 of the elastic valve member 5 is turned partially inside out and fastened to a lower portion of the rigid tubular casing 4 as illustrated.

Because the lower diaphragm portion 7 of the elastic valve member 5 is turned partially inside out and attached within a lower portion of the rigid tubular casing in an inverted manner, potential energy is stored in the hemi-toroidal part of the rolling diaphragm. Because of the stored potential energy, the rolling diaphragm will move toward the position with less stored energy in which the thinnest wall portion adjacent the inner wall of the rigid tubular casing is bent to the hemi-toroidal shape. If the rolling diaphragm is constrained by the upper portion 6 of the elastic valve member 5, it will exert a force which is a function of the difference in wall thickness from one side of the curved portion of the rolling diaphragm to the other. The wall thickness variation required to create a given force curve may thus be determined as discussed below. A typical shape of the lower diaphragm portion 7 of the elastic valve member 5 is graphed in FIG. 6, with the corresponding desired typical force curve shown in FIG. 5.

The elastic valve element, including the upper and lower diaphragm portion may be made of any suitable elastic material which is biocompatible and resistant to a urine environment. Preferred materials include latex rubbers, silicone rubbers and polyurethane, with silicone rubbers being the material most preferred.

Figure 5:
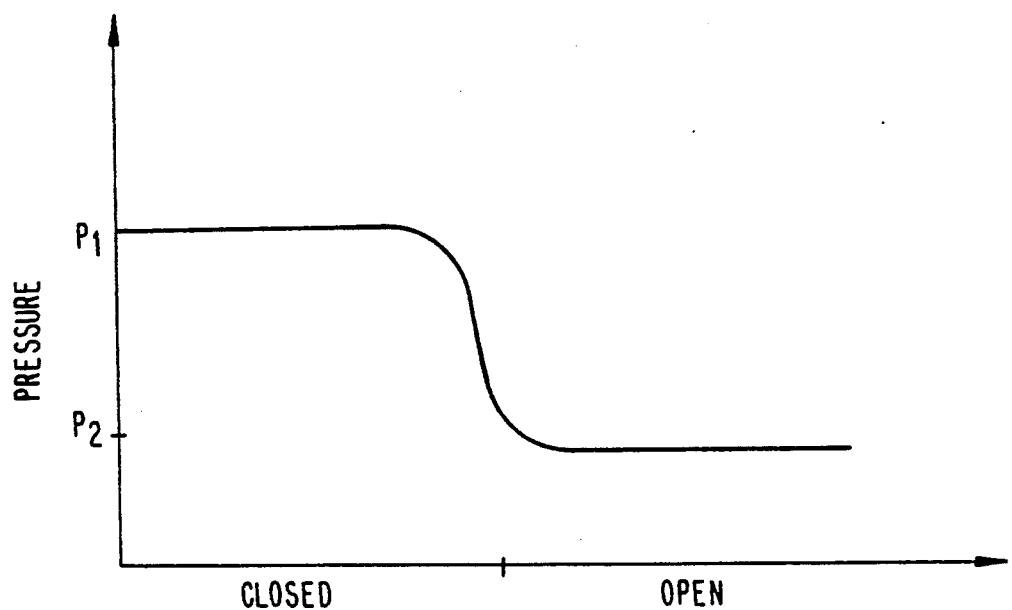
FIG. 5 is a diagram illustrating the relationship between the position of the lower diaphragm portion of the valve element and the bladder pressure exerted upon the lower diaphragm portion of the valve element.

The necessary wall thickness including the tapering of the lower diaphragm portion 7 of the elastic valve member 5 is determined as follows. First, the desired pressures required to operate the valve assembly are determined. FIG. 5 illustrates the relationship between the pressure exerted by the bladder on the lower diaphragm portion 7 of the elastic valve member and the open and closed positions of the valve assembly. $P_1$ in FIG. 5 represents the bladder pressure at which the valve is to be maintained in the closed position. In order to prevent non-voluntary discharge of the bladder $P_1$ is selected to be in the range of about 10 to 20 percent greater than normal bladder pressure. $P_2$ as illustrated in FIG. 5 corresponds to the valve assembly being in the open position. In order to prevent a patient from having to exert and maintain excessive pressures during discharge, $P_2$ is selected to be in a range which is easily maintainable during discharge, which may be about 30 to 80 percent of $P_1$. As indicated in FIG. 5, there is a transition range wherein pressure is applied or removed to open and close the valve.

Figure 6:
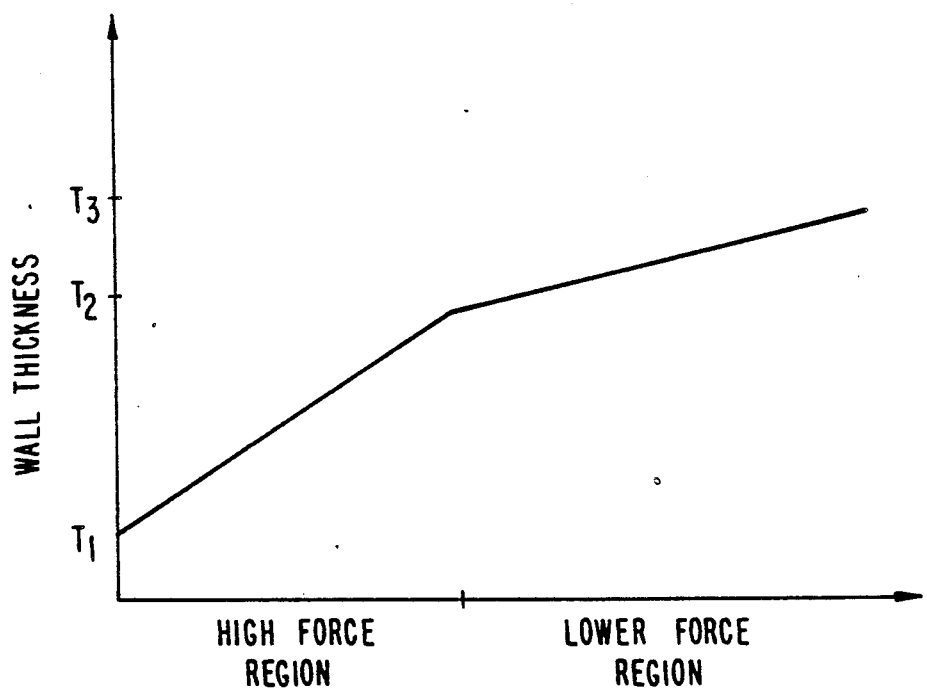
FIG. 6 is a diagram illustrating the relationship between the force created by the valve element and the wall thickness of the valve element.

Once the values of $P_1$ and $P_2$ are determined, the wall thickness of the lower diaphragm portion 7 of the elastic valve member 5 may be determine. FIG. 6 illustrates the relationship between the force acting upon the lower diaphragm portion of the elastic valve element and the wall thickness thereof. In FIG. 6 the slope of the curve from $T_1$ to $T_2$ represents the higher force which is required to initially open the valve member for discharge of the bladder. As discussed above, the pressure required to open the valve may be selected to be in the range of about 10 to 20 percent greater than normal bladder pressure. Therefore, the initial thickness of the lower diaphragm portion of the elastic valve element from $T_1$ to $T_2$ should have a greater slope to provide a greater force region. The relative thickness of $T_1$ and $T_2$ are best illustrated in FIG. 2 where the position of $T_2$ is merely illustrative. The pressure required to easily discharge fluid from the bladder should be selected to be in a range which is easily maintainable during discharge, which may be about 30 to 80 percent of $P_2$ as described above. Therefore, the thickness of the lower diaphragm portion of the elastic valve element from $T_2$ to $T_3$ should have a lesser slope to provide a lesser force region. The relative thickness of $T_2$ and $T_3$ are best illustrated in FIG. 2 where the position of $T_2$ is merely illustrative. As indicated above, Elastic Strain theory can be utilized to determined the amount of potential energy stored in the hemi-toroidal part of the rolling diaphragm. Since the force exerted by the rolled diaphragm is a function of the difference in wall thickness from one side of its curve d shape to the other, the appropriate wall thickness may be determined so as to provide a desired force which is applied to the upper portion 6 of the elastic valve member 5.

It is noted that any selected elastic material from which the elastic valve member is made will have a particular wall thickness which is dependent upon the elastic characteristics of the material. However, the manner by which to determine the appropriate wall thickness is the same for any selected material.

In operation, the lower diaphragm portion 7 of the elastic valve member 5 normally provides enough upward force to cause the upper portion 6 of the elastic valve member 5 to deform or "kink" so as to occlude its central channel shown at 12. This is the normal closed state of the prosthetic valve assembly 1, as illustrated in FIG. 1. Bladder pressure rises gradually as the bladder 3 fills, but will not normally cause sufficient pressure to open the central channel 12 of the upper portion 6 of the elastic valve member 5. Also, momentary elevation of bladder pressure due to coughing, jumping, spasmodic bladder contraction, or the like, will not open the central channel 12.

The patient may raise abdominal and hence bladder pressure voluntarily and sustain it for a substantial duration, sufficient to overcome the stored energy in the lower diaphragm portion 7 of the elastic valve member 5 and cause the lower diaphragm portion 7 to "unroll" as illustrated in FIG. 4, which illustrates the open position of the prosthetic valve assembly 1. A patient may provide the necessary pressure by increasing intra-abdominal pressure by performing a "Valsalva" maneuver (such as in straining at stool), or by action somewhat similar to normal urination. A sufficiently high bladder pressure may be perhaps about 30 cm $H_2O$ and a suitable duration of time to maintain such pressure may be about 5 seconds.

FIG. 3 illustrates the closed position of the central passage 12 and the arrangement of the petal retention members 8.

As illustrated in FIG. 4, when the lower diaphragm portion 7 of the elastic valve member 5 "unrolls" into the open position, the central passage 12 of the upper portion 6 of the elastic valve member 5 straightens and becomes "unkinked" so as to provide for an unobstructed flow path for discharge of fluids from the bladder.

In the open position, only a slight force will be required to keep the valve open, since the change in wall thickness from one side of the hemi-toroid to the other in this position is small by design. However, this small force is enough to slowly close the valve once voluntary opening pressure is removed. Once the valve is closed again, the larger force holds it closed until the cycle is repeated.

Although the present invention has been described with reference to particular means, materials and embodiments, from the foregoing description, one skilled in the art can ascertain the essential characteristics of the present invention and various changes and modifications may be made to adapt the various uses and characteristics thereof without departing from the spirit and scope of the present invention as described in the claims which follow.

I claim:

1. A prosthetic urethral sphincter valve comprising:
   a rigid tubular casing means for positioning in a patient's urethra, said rigid tubular casing means having a longitudinal axis and a top end means for location adjacent and exposure to the patient's bladder; and
   an elastic valve member located within said rigid tubular casing means which comprises an upper means which forms a central tubular passage which extends along the length of said rigid tubular casing means and is opened or closed depending on the alignment thereof, and a lower diaphragm means comprising a rolling diaphragm, for providing a stored potential energy which normally provides enough upward force to cause the upper means to deform so as to align the central tubular passage to be closed, but which force may be overcome by the patient voluntarily raising bladder pressure for a predetermined duration so that the upper means aligns the central tubular passage to be open.

2. A prosthetic urethral sphincter valve according to claim 1, wherein said lower diaphragm means includes an end which is attached to said rigid tubular casing means and said lower diaphragm means of said elastic valve member comprises a wall which tapers from said upper means of said elastic valve member to the end of said lower diaphragm means which is attached to said rigid tubular casing means.

3. A prosthetic urethral sphincter valve according to claim 2, wherein said wall of said lower diaphragm means comprises two successive tapered portions which extend in the same direction and which provide different amounts of stored potential energy in said lower diaphragm means depending on the position of said lower diaphragm means.

4. A prosthetic urethral sphincter valve according to claim 1, wherein an annular region is defined between said rigid tubular casing means and said elastic valve member, said annular region being filled with a viscous fluid.

5. A prosthetic urethral sphincter valve according to claim 4, wherein said viscous fluid comprises a viscous grease.

6. A prosthetic urethral sphincter valve according to claim 1 further comprising means for retaining said prosthetic urethral sphincter valve in position in the patient's bladder.

7. A prosthetic urethral sphincter valve according to claim 6, wherein said means for retaining said prosthetic urethral sphincter valve comprises outwardly biased resilient retaining petal means on the top end means of said rigid tubular casing means for retentively engaging the patient's bladder.

8. A prosthetic urethral sphincter valve according to claim 1, wherein said upper means and said lower diaphragm means of said elastic valve member are integral.

9. A prosthetic urethral sphincter valve according to claim 8 wherein said elastic valve member is made from a silicon rubber material.

10. A prosthetic urethral sphincter valve which comprises:
a rigid tubular casing means for positioning in a patient's urethra, said rigid tubular casing means having a longitudinal axis and top end means for location adjacent and exposure to the patient's bladder; and
an integral elastic valve member located within said rigid tubular casing means which defines a central tubular passage means which extends along the length of said rigid tubular casing means and is opened or closed depending on the alignment thereof, means for aligning the central passage means to cause such to open upon application of a first bladder pressure $P_1$ voluntarily exerted by the patient and means to maintain said central passage open by the application of a second bladder pressure $P_2$ voluntarily exerted by the patient, wherein $P_1 > P_2$.

11. A prosthetic urethral sphincter valve according to claim 10, wherein an annular region is defined between said rigid tubular casing means and said elastic valve member, said annular region being filled with a viscous fluid.

12. A prosthetic urethral sphincter valve according to claim 11, wherein said viscous fluid comprises a viscous grease.

13. A prosthetic urethral sphincter valve according to claim 10 further comprising means for retaining said prosthetic urethral sphincter valve in position in the patient's bladder.

14. A prosthetic urethral sphincter valve according to claim 13, wherein said means for retaining said prosthetic urethral sphincter valve comprises outwardly biased resilient retaining petal means on the top end means of said rigid tubular casing means for retentively engaging the patient's bladder.

15. A method of controlling urinary continence of a patient with a prosthetic urethral sphincter valve as claimed in claim 1 which comprises the following steps:
positioning the rigid tubular casing means in the patient's urethra with the top end means located adjacent and exposed to the patient's bladder and exerting bladder pressure voluntarily by the patient for a predetermined duration which overcomes the stored potential energy and aligns the central tubular passage thereby opening the same.

16. A method of controlling urinary continence of a patient according to claim 15 further comprising retaining said prosthetic urethral sphincter valve in position in the patient's urethra.

* * * * *